United States Patent
Schellen et al.

(10) Patent No.: US 8,557,880 B2
(45) Date of Patent: Oct. 15, 2013

(54) MULTI-STAGE ADIABATIC METHOD FOR PERFORMING THE FISCHER-TROPSCH SYNTHESIS

(75) Inventors: Ralph Schellen, Dormagen (DE); Leslaw Mleczko, Dormagen (DE); Evin Hizaler Hoffmann, Köln (DE); Stephan Schubert, League City, TX (US); Rushikesh Apte, Düsseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 206 days.

(21) Appl. No.: 13/140,253

(22) PCT Filed: Dec. 4, 2009

(86) PCT No.: PCT/EP2009/008671
§ 371 (c)(1),
(2), (4) Date: Jun. 16, 2011

(87) PCT Pub. No.: WO2010/069486
PCT Pub. Date: Jun. 24, 2010

(65) Prior Publication Data
US 2012/0136076 A1 May 31, 2012

(30) Foreign Application Priority Data
Dec. 20, 2008 (DE) .......................... 10 2008 064 282

(51) Int. Cl.
*C07C 27/00* (2006.01)

(52) U.S. Cl.
USPC ........................................... 518/705; 518/700

(58) Field of Classification Search
USPC .................................................... 518/700, 705
See application file for complete search history.

(56) References Cited

U.S. PATENT DOCUMENTS

| | | | |
|---|---|---|---|
| 2,503,356 | A | 4/1950 | Sensel et al. |
| 2,680,125 | A | 6/1954 | Wilhelm |
| 6,211,255 | B1 | 4/2001 | Schanke et al. |
| 6,558,634 | B1 | 5/2003 | Wang et al. |
| 6,784,212 | B2 | 8/2004 | Steynberg et al. |

FOREIGN PATENT DOCUMENTS

| | | |
|---|---|---|
| EP | 0 823 470 A1 | 2/1998 |
| EP | 1 251 951 A | 10/2002 |
| GB | 2 444 055 A | 5/2008 |
| WO | 2005 075606 A1 | 8/2005 |
| WO | 2008 080357 A1 | 7/2008 |

OTHER PUBLICATIONS

Van Dijk et al, A mechanistic study of the FischerTropsch snthesis using transient isotopic tracing Part 2 Model quantification, Topics in Cat 26(1) 2003, 163-171.

*Primary Examiner* — Jafar Parsa
(74) *Attorney, Agent, or Firm* — Norris McLaughlin & Marcus, P.A.

(57) ABSTRACT

The present invention relates to a multistage adiabatic process for performing the Fischer-Tropsch synthesis at low temperatures, in which the synthesis is performed in 5 to 40 series-connected reaction zones under adiabatic conditions.

17 Claims, 2 Drawing Sheets

MULTI-STAGE ADIABATIC METHOD FOR PERFORMING THE FISCHER-TROPSCH SYNTHESIS

This application is a 371 of PCT/EP2009/008671, filed Dec. 4, 2009, which claims foreign priority benefit under 35 U.S.C. § 119 of the German Patent Application No. 10 2008 064 282.7 filed Dec. 20, 2008, the disclosures of which are incorporated herein by reference.

The present invention relates to a multistage adiabatic process for performing the Fischer-Tropsch synthesis at low temperatures, in which the synthesis is performed in 5 to 40 series-connected reaction zones under adiabatic conditions.

The Fischer-Tropsch synthesis is a chemical synthesis route which has become common knowledge and allows the preparation of hydrocarbons from carbon monoxide and hydrogen. Especially in recent times, increasing significance is being ascribed to this synthesis route, since global resources of natural hydrocarbons in the form of mineral oils or waxes are becoming increasingly scarce. Carbon monoxide and hydrogen are, however, available in a relatively large amount, or are obtained as by-products in connection with other processes or can be prepared selectively, without necessarily needing to resort to the aforementioned natural resources.

A distinction is nowadays generally drawn between two basic subgroups of the Fischer-Tropsch synthesis. One is the low-temperature process variant, and the other the high-temperature process variant.

The present invention relates, as already described, to the low-temperature process variant. The two process variants are distinguished, in addition to temperature, in particular by the products obtained from the process variants. While predominantly shorter-chain liquid or gaseous hydrocarbons are obtained in the high-temperature process variant, predominantly longer-chain liquid hydrocarbons, some of them of high viscosity, are obtained in the low-temperature process variant.

The low-temperature process variant is generally advantageous in that the shorter-chain hydrocarbons of the high-temperature process variant can also be obtained from the longer-chain hydrocarbons by the process of "cracking" which is common knowledge to those skilled in the art, but the longer-chain hydrocarbons at the same time constitute starting materials for higher-value products such as waxes.

A fundamental problem in both process variants of the Fischer-Tropsch synthesis is the strongly exothermic character of the synthesis, such that, in terms of process technology, high demands are made on the removal of the heat from the synthesis when the desire is to control the synthesis exactly. As already described above, the temperature has a strong influence on the product properties from the Fischer-Tropsch synthesis. When the desire is thus to obtain a specific fraction of the hydrocarbons with a defined chain length, the temperatures under which the process is performed should be established and controlled particularly exactly.

In addition, there is the general problem that, in the event of a locally excessive temperature ("hot spot"), the formation of methane as an undesired by-product is favoured.

This fact is also disclosed in U.S. Pat. No. 6,558,634 which further discloses a catalyst and a process for performing the Fischer-Tropsch synthesis, in which a multilayer catalyst of porous structure is used, on the surface of which a Fischer-Tropsch catalyst is immobilized. The process according to U.S. Pat. No. 6,558,634 is performed at temperatures above 200° C.; it is preferably performed at temperatures of 200° C. to 300° C. It is further disclosed that a gas mixture comprising hydrogen and carbon monoxide with a molar ratio of hydrogen to carbon monoxide of 1:1 to 6:1 can be used to perform the synthesis. The average contact time of the gas mixture with the catalyst is, according to U.S. Pat. No. 6,558,634, preferably less than 5 s.

The process according to the disclosure of U.S. Pat. No. 6,558,634 is performed in a reactor with reactor walls which are in contact with a cooling chamber, such that the reaction zone in which the Fischer-Tropsch synthesis is performed is cooled. The reaction zone of the process according to U.S. Pat. No. 6,558,634 is thus not adiabatic.

The process according to the disclosure of U.S. Pat. No. 6,558,634 is disadvantageous since the reaction zones are cooled via the walls of the chamber containing the reaction zone, thus attempting to enable the necessary temperature control of the process. Cooling via a chamber wall leads to the effect that a temperature profile is established along the flow direction of the process gases carbon monoxide and hydrogen in a reaction zone owing to the exothermic character of the reaction, since a constant heat flow is removed from the reaction zone via the surface of the chamber wall, which has to be regulated via the temperature and the heat capacity, and possibly via the flow rate of the heat carrier medium in the cooling chamber. The aforementioned temperature profile thus inevitably arises, such that local excessive temperatures ("hot spots") cannot be prevented reliably, and the associated adverse effects, for instance enhanced formation of methane, occur. Moreover, a possible failure of the cooling capacity would be equivalent to an immediate, uncontrollable temperature rise in the reaction zone of the Fischer-Tropsch synthesis, which can also lead to safety problems. Cooling by the parallel process variant, which is nevertheless performed in one stage in flow direction, according to the disclosure of U.S. Pat. No. 6,558,634 is not envisaged.

U.S. Pat. No. 6,211,255 discloses an alternative embodiment of a process for performing the Fischer-Tropsch synthesis, in which hydrogen and carbon monoxide flow through a monolithic catalyst at temperatures of 195° C. or 210° C. The process of U.S. Pat. No. 6,211,255 is further characterized in that hydrogen and carbon monoxide are conducted in cocurrent over the monolithic catalyst. The liquid hydrocarbons which form are conducted in a circulation stream and cooled in this circulation stream. Only a portion of the circulation stream is conducted out of the process as product. Temperature control of the process gas stream of hydrogen and/or carbon monoxide is not disclosed. Moreover, the process is one-stage with regard to the process gases.

The process according to U.S. Pat. No. 6,211,255 is disadvantageous because, as described above, temperature control of the Fischer-Tropsch synthesis is possible only by means of cooling of the liquid hydrocarbon. No other influence on the temperature in the reaction zone is envisaged. It follows that the establishment of a temperature profile and the negative effects resulting therefrom cannot be prevented.

A further process variant comprising a Fischer-Tropsch synthesis is disclosed in U.S. Pat. No. 6,784,212. Here, a process gas comprising carbon monoxide and hydrogen is first obtained from natural gas, and is then fed to the Fischer-Tropsch synthesis. According to the process of U.S. Pat. No. 6,784,212, this Fischer-Tropsch synthesis is performed at temperatures of 200° C. to 380° C. at pressures of 1 to 100 bar in tubular fixed bed reactors or "slurry reactors", the latter being known to the person skilled in the art as apparatuses in which liquid phases are present, in which finely dispersed solid is present and through which a process gas can be conducted. The exact mode of operation of the Fischer-Tropsch synthesis in relation to any adiabatic character is not disclosed. In contrast, the upstream preparation of carbon monoxide and hydrogen is described as adiabatic. According to U.S. Pat. No. 6,784,212, it is possible with supply of further hydrogen to perform the Fischer-Tropsch synthesis in two stages.

For lack of disclosure in U.S. Pat. No. 6,784,212 with regard to possible temperature control in the performance of the Fischer-Tropsch synthesis, such a process is just as disadvantageous as the above-described processes according to U.S. Pat. No. 6,558,634 and U.S. Pat. No. 6,211,255.

An alternative process variant which likewise enables a certain control of temperature is disclosed in WO 2005/075606. In this case, the temperature control is achieved through a multitude of parallel microchannels and high surface-to-volume ratios. Again, the reaction chambers are in contact with cooling chambers through which a heat carrier medium flows. This gives rise in principle to the analogous disadvantages as have already been detailed in this regard in connection with the disclosure of U.S. Pat. No. 6,558,634. However, the temperature control of the process according to WO 2005/075606 is advantageous over the latter, since, as just stated, the surface area in contact with the process gases hydrogen and carbon monoxide is considerably greater compared to the volume of the particular reaction zone, such that the development of a profile is not prevented, but the extent thereof can certainly be reduced significantly.

However, the process according to WO 2005/075606 is disadvantageous because failure of the cooling circuit can result in the same operating states which are disadvantageous from a safety point of view which are also a risk in the case of U.S. Pat. No. 6,558,634. No further cooling means is provided. Moreover, the advantageous surface-to-volume ratio is obtained by simultaneously tolerating an immensely enhanced pressure drop through the significant reduction in the free flow cross section of each and every reaction zone. The energy needed to convey the process gases through the reaction zone thus likewise grows considerably. Moreover, the formation of high-viscosity hydrocarbons at sites of quite low temperature in the reaction zone can lead to blockage of the free cross section, which would stop the process.

EP 1 251 951 (B1) discloses an apparatus and the means of performing chemical reactions in the apparatus, the apparatus being characterized by a cascade of mutually contacting reaction zones and heat exchanger apparatuses which are arranged cohesively joined to one another in an integrated system. The process to be performed therein is thus characterized by the contact of the different reaction zones with a particular heat exchanger apparatus in the form of a cascade.

There is no disclosure with regard to usability of the apparatus and of the process for the synthesis of liquid hydrocarbons from carbon monoxide and hydrogen. More particularly, applicability to polyphasic reaction systems in general is not disclosed.

It thus remains unclear how, proceeding from the disclosure of EP 1 251 951 (B1), such a reaction is to be performed by means of the apparatus and of the process performed therein. Moreover, for reasons of unity of invention, it has to be assumed that the process disclosed in EP 1 251 951 (B1) is performed in an apparatus identical or similar to the disclosure with regard to the apparatus. The result of this is that, due to the large-area contact of the heat exchange zones with the reaction zones according to the disclosure, a significant amount of heat is transferred by conduction of heat between the reaction zones and the adjacent heat exchange zones.

The disclosure with regard to the oscillating temperature profile can thus only be understood in such a way that the temperature peaks found here would be greater if this contact were not to exist.

EP 1 251 951 (B1) thus discloses multistage processes in cascades of reaction zones, from which heat is removed in an undefined amount by conduction of heat. Accordingly, the process disclosed is disadvantageous in that exact temperature control of the process gases of the reaction is impossible.

Proceeding from the prior art, it would therefore be advantageous to provide a process for preparing liquid hydrocarbons from carbon monoxide and hydrogen, which can be performed in simple reaction apparatus and which enables exact, simple temperature control, such that it allows high conversions at maximum purities of the product.

For the preparation of liquid hydrocarbons from carbon monoxide and hydrogen, as just described, no suitable processes which are capable of solving the aforementioned problems in their entirety have been disclosed to date.

It is therefore an object of the invention to provide a process for preparing liquid hydrocarbons from carbon monoxide and hydrogen, which is performable with exact temperature control in simple reaction apparatus and which, as a result, allows high conversions at high purities of the product, the heat of reaction being utilizable either for the benefit of the reaction or in another way.

It has been found that, surprisingly, a process for preparing liquid hydrocarbons from the process gases carbon monoxide and hydrogen, comprising a Fischer-Tropsch synthesis in the presence of heterogeneous catalysts, characterized in that it is performed in 5 to 40 series-connected reaction zones in which the heterogeneous catalysts are present under adiabatic conditions at temperatures of 220° C. to 300° C., achieves this object.

In the context of the present invention, carbon monoxide refers to a process gas which comprises essentially carbon monoxide. Typically, the proportion of carbon monoxide in the process gas fed to the process, referred to as carbon monoxide, is between 70 and 100% by weight, preferably between 80 and 100% by weight.

In the context of the present invention, hydrogen refers to a process gas which comprises essentially hydrogen. Typically, the proportion of hydrogen in the process gas fed to the process, referred to as hydrogen, is between 90 and 100% by weight, preferably between 95 and 100% by weight.

In addition to the essential hydrogen component of the process gas, it may also comprise secondary components. Non-exclusive examples of secondary components which may be present in the process gas are, for instance, argon, nitrogen and/or carbon dioxide. The same applies in the case of the carbon monoxide process gas.

The two process gases, hydrogen and carbon monoxide, together with their particular components, are also referred to collectively in the context of the present invention as the process gas.

In general, in the context of the present invention, the process gas is thus understood to mean a gas mixture which comprises hydrogen, carbon monoxide and secondary components.

In the context of the present invention, liquid hydrocarbons refer to aliphatic hydrocarbons which are present in the liquid phase in the reaction zones under the conditions of the process. Typically, these are aliphatic hydrocarbons comprising at least nine carbon atoms, preferably comprising at least 12 carbon atoms.

According to the invention, the performance of the process under adiabatic conditions means that essentially no heat is supplied actively to, nor heat is withdrawn from, the reaction zone from the outside. It is common knowledge that complete insulation from heat supply or removal is possible only by complete evacuation with exclusion of the possibility of heat transfer by radiation. In the context of the present invention, "adiabatic" therefore means that no measures for heat supply or removal are taken.

In an alternative embodiment of the process according to the invention, however, heat transfer can be reduced, for example, by insulation by means of commonly known insulators, for example polystyrene insulating materials, or else by sufficiently large distances from heat sinks or heat sources, in which case the insulator is air.

One advantage of the inventive adiabatic method with 5 to 40 series-connected reaction zones over a non-adiabatic method is that there is no need to provide any means of heat removal in the reaction zones, which implies a considerable simplification of the construction. This gives rise more particularly to simplifications in the manufacture of the reactor and in the scalability of the process, and an enhancement of the reaction conversions. Moreover, the heat generated in the course of progression of the exothermic reaction can be utilized in a controlled manner to enhance the conversion in the individual reaction zone.

A further advantage of the process according to the invention is the possibility of very exact temperature control through the close graduation of adiabatic reaction zones. It is thus possible to establish and control a temperature which is advantageous in the progression of the reaction in each reaction zone.

The catalysts used in the process according to the invention are typically catalysts consisting of a material which, in addition to its catalytic activity for the reaction according to formula (I), is characterized by sufficient chemical resistance under the conditions of the process and by a high specific surface area.

Catalyst materials characterized by such a chemical resistance under the conditions of the process are, for example, catalysts which comprise oxides of aluminium, titanium, zirconium and/or silicon, and/or oxides of lanthanoids. These materials are usually supports of the catalyst materials, to which the active constituents of the catalyst are applied.

Suitable active constituents of the catalysts are, for instance, cobalt compounds as already known to the person skilled in the art and/or compounds which comprise nickel, platinum and/or palladium. In preferred embodiments, they may also be doped with magnesium oxide as a promoter.

In the context of the present invention, specific surface area refers to the area of the catalyst material which can be reached by the process gas, based on the mass of catalyst material used.

A high specific surface area is a specific surface area of at least 1 $m^2/g$, preferably of at least 10 $m^2/g$.

The inventive catalysts are each present in the reaction zones and may be present in all manifestations known per se, for example fixed bed, moving bed.

Preference is given to the fixed bed manifestation.

The fixed bed arrangement comprises a catalyst bed in the actual sense, i.e. loose, supported or unsupported catalyst in any form, and in the form of suitable packings. The term "catalyst bed" as used here also includes continuous regions of suitable packings on a support material or structured catalyst supports. These would be, for example, ceramic honeycomb supports or foams which are to be coated and have comparatively high geometric surface areas, or corrugated layers of metal wire mesh on which, for example, catalyst granules are immobilized. In the context of the present invention, a special form of packing is considered to be the presence of the catalyst in monolithic form.

When a fixed bed arrangement of the catalyst is used, the catalyst is preferably present in beds of particles with mean particle sizes of 1 to 10 mm, preferably 1.5 to 8 mm, more preferably of 2 to 6 mm.

Likewise preferably, the catalyst is present in fixed bed arrangement in monolithic form.

When a catalyst in monolithic form is used in the reaction zones, in a preferred development of the invention, the catalyst present in monolithic form is provided with channels through which the process gases flow. Typically, the channels have a diameter of 0.1 to 3 mm, preferably a diameter of 0.2 to 2 mm, more preferably of 0.5 to 1 mm.

When a moving bed arrangement of the catalyst is used, the catalyst is present preferably in loose beds of particles as have already been described in the context of the fixed bed arrangement.

Beds of such particles are advantageous because the particles possess a high specific surface area of the catalyst material with respect to the process gases, and hence a high conversion rate can be achieved. The mass transfer limitation of the reaction by diffusion can thus be minimized. At the same time, the particles are thus, however, still not sufficiently small as to result in a disproportionate increase in pressure drops in the course of flow through the fixed bed. The ranges of the particle sizes specified in the preferred embodiment of the process, comprising a reaction in a fixed bed, are thus an optimum between the achievable conversion and the pressure drop obtained in the course of performance of the process. Pressure drop is directly coupled to the energy needed in the form of pump and/or compressor power, such that a disproportionate increase thereof would result in an uneconomic mode of operation of the process.

In a preferred embodiment of the process according to the invention, the conversion is effected in 7 to 30 and more preferably 10 to 20 series-connected reaction zones.

A preferred further embodiment of the process is characterized in that downstream of at least one reaction zone is at least one heat exchange zone through which the process gas leaving at least one of those reaction zones is passed. The process gas and the liquid hydrocarbons are preferably passed through at least one heat exchange zone connected downstream of this reaction zone.

In a particularly preferred further embodiment of the process, downstream of each reaction zone is at least one, preferably exactly one, heat exchange zone through which at least the process gas leaving the reaction zone, preferably together with the liquid hydrocarbons, is passed.

The reaction zones may either be arranged in one reactor or arranged divided between a plurality of reactors. The arrangement of the reaction zones in one reactor leads to a reduction in the number of the apparatuses used.

The individual reaction zones and heat exchange zones can also be arranged together in one reactor or divided between several reactors in any combinations of reaction zones with heat exchange zones in each case.

When reaction zones and heat exchange zones are present in one reactor, in an alternative embodiment of the invention, there is a thermal insulation zone between them in order to be able to maintain the adiabatic operation of the reaction zone.

In addition, individual series-connected reaction zones may independently also be replaced or supplemented by one or more parallel-connected reaction zones. The use of parallel-connected reaction zones allows, more particularly, the exchange or addition thereof in the course of running continuous overall operation of the process.

Parallel- and series-connected reaction zones can especially also be combined with one another. However, the process according to the invention more preferably has exclusively series-connected reaction zones.

The reactors used with preference in the process according to the invention may consist of simple vessels with one or more reaction zones, as described, for example, in Ullmanns Encyclopedia of Industrial Chemistry (Fifth, Completely Revised Edition, vol. B4, page 95-104, page 210-216), in which case thermal insulation zones may additionally be provided in each case between the individual reaction zones and/or heat exchange zones.

In an alternative embodiment of the process, there is thus at least one thermal insulation zone between a reaction zone and a heat exchange zone. There is preferably a thermal insulation zone around each reaction zone.

The catalysts or the fixed beds thereof are installed in a manner known per se on or between gas- and liquid-permeable walls comprising the reaction zone of the reactor. Especially in the case of thin fixed beds, technical devices for homogeneous gas distribution can be installed upstream of the catalyst beds in flow direction. These may be perforated sheets, bubble-cap trays, valve trays or other internals which bring about homogeneous entry of the process gas into the fixed bed by generating a low but homogeneous pressure drop.

In a preferred embodiment of the process, the inlet temperature of the process gas entering the first reaction zone is from 10 to 260° C., preferably from 50 to 250° C., more preferably from 150 to 235° C.

In a further preferred embodiment of the process, the absolute pressure at the inlet to the first reaction zone is between 10 and 70 bar, preferably between 20 and 50 bar, more preferably between 25 and 40 bar.

In yet a further preferred embodiment of the process, the residence time of the process gas in all reaction zones together is between 10 and 700 s, preferably between 20 and 500 s, more preferably between 150 and 250 s. At the same time, the residence time of the liquid hydrocarbons in all reaction zones together is between 50 and 2500 s, preferably between 100 and 1500 s, more preferably between 600 and 900 s.

The process gas is preferably fed in only upstream of the first reaction zone. This has the advantage that all of the process gas can be utilized for the absorption and removal of the heat of reaction in all reaction zones. Moreover, such a procedure can enhance the space-time yield, or reduce the catalyst mass needed. However, it is also possible to meter further hydrogen into the process gas if required upstream of one or more of the reaction zones which follow downstream of the first reaction zone. The supply of the hydrogen process gas between the reaction zones additionally allows the temperature and the conversion to be controlled.

In a preferred embodiment of the process according to the invention, the process gas is cooled downstream of at least one of the reaction zones used, more preferably downstream of each reaction zone. Within this preferred embodiment, it is particularly preferred in each case also to cool the liquid hydrocarbons at the same time.

To this end, the process gas, after it leaves a reaction zone, is passed through one or more of the abovementioned heat exchange zones downstream of the particular reaction zones. These may be configured as heat exchange zones in the form of the heat exchangers known to those skilled in the art, for example tube bundle heat exchangers, plate heat exchangers, annular groove heat exchangers, spiral heat exchangers, thin-tube heat exchangers and/or microstructured heat exchangers. The heat exchangers are preferably microstructured heat exchangers.

In the context of the present invention, "microstructured" means that the heat exchanger, for the purpose of heat transfer, comprises fluid-conducting channels which are characterized in that they have a hydraulic diameter between 50 μm and 5 mm. The hydraulic diameter is calculated from four times the flow cross-sectional area of the fluid-conducting channel divided by the circumference of the channel.

In a particular embodiment of the process, as the process gas and/or liquid hydrocarbon is cooled in the heat exchange zones by the heat exchanger, steam is raised.

Within this particular embodiment, preference is given to performing an evaporation, preferably partial evaporation, in the heat exchangers which include the heat exchange zones on the side of the cooling medium.

In the context of the present invention, "partial evaporation" refers to an evaporation in which a gas/liquid mixture of a substance is used as a cooling medium, and a gas/liquid mixture of a substance is also still present after heat transfer in the heat exchanger.

The performance of an evaporation is particularly advantageous because the achievable heat transfer coefficient from/to process gas to/from cooling/heating medium is particularly high and hence efficient cooling can be achieved as a result.

The performance of a partial evaporation is particularly advantageous because the absorption/release of heat by the cooling medium, as a result, no longer results in a temperature change in the cooling medium, but the gas/liquid equilibrium is merely shifted. The consequence of this is that the process gas is cooled against a constant temperature over the entire heat exchange zone. This in turn reliably prevents the occurrence of radial temperature profiles in the flow of the process gas, which improves the control over the reaction temperatures in the reaction zones and more particularly prevents the development of local overheating as a result of radial temperature profiles.

In an alternative embodiment, instead of an evaporation/partial evaporation, it is also possible to provide a mixing zone upstream of the inlet of a reaction zone, in order to homogenize any radial temperature profiles which arise in the course of cooling in the flow of the process gas through mixing transverse to the principle flow direction.

In a preferred embodiment of the process, the series-connected reaction zones are operated with an average temperature rising or falling from reaction zone to reaction zone. This means that, within a sequence of reaction zones, the temperature can be allowed either to rise or fall from reaction zone to reaction zone. This can be established, for example, via the control of the heat exchange zones connected between the reaction zones. Further means of establishing the average temperature are described hereinafter.

The thickness of the reaction zones through which the flow proceeds may be selected identically or differently, and is determined according to the laws which are common knowledge to those skilled in the art from the above-described residence time and the amounts of process gas throughput in the process in each case.

The mass flow throughputs of liquid hydrocarbons possible by the process in accordance with the invention, from which the amounts of the process gases hydrogen and carbon monoxide to be used are also calculated, are typically between 100 and 200 t/h, preferably between 10 and 170 t/h, more preferably between 70 and 100 t/h.

The maximum outlet temperature of the process gas from the reaction zones is typically within a range from 220° C. to 300° C., preferably from 240° C. to 280° C., more preferably from 250° C. to 260° C. The temperature in the reaction zones is preferably controlled by at least one of the following measures: selecting the dimensions of the adiabatic reaction zone, controlling the removal of heat between the reaction zones, adding process gas between the reaction zones, molar ratio of the reactants/excess of hydrogen used, addition of inert gases, especially nitrogen, carbon dioxide, upstream of and/or between the reaction zones.

The composition of the catalysts in the inventive reaction zones may be the same or different. In a preferred embodiment, the same catalysts are used in each reaction zone. However, it is also possible advantageously to use different catalysts in the individual reaction zones. For instance, especially in the first reaction zone, when the concentration of hydrogen and carbon monoxide is still high, a less active catalyst can be used, and, in the further reaction zones, the activity of the catalyst can be increased from reaction zone to reaction zone. The catalyst activity can also be controlled by diluting with inert materials or support material. It is likewise advantageous to use a catalyst in the first and/or second reaction zone, said catalyst being particularly stable to deactivation at the temperatures of the process in these reaction zones.

The process according to the invention can prepare, per 1 m$^3$ of reaction zone volume, 5 kg/h to 100 kg/h, preferably 20 kg/h to 80 kg/h, more preferably 25 kg/h to 50 kg/h, of liquid hydrocarbons.

The process according to the invention thus features high space-time yields, combined with a reduction in the apparatus sizes and a simplification of the apparatuses or reactors. This surprisingly high space-time yield is enabled by the interplay of the inventive and preferred embodiments of the novel process. Especially the interplay of graduated adiabatic reaction zones with heat exchange zones inbetween and the defined residence times enables exact control of the process and the resulting high space-time yields.

The present invention is illustrated by the figures, but without being restricted thereto.

The present invention is further illustrated in detail with reference to the examples which follow, without being restricted thereto.

EXAMPLES

Example 1

In this example, a process gas consisting of hydrogen and carbon monoxide with a molar ratio of 2.15 to 1 flows into a first of a total of 12 fixed catalyst beds composed of a monolithic cobalt catalyst which is supported on aluminium oxide and has a channel diameter of 0.75 mm. The process thus comprises 12 reaction zones. The catalyst is present in the reaction zones in a proportion of 25% by volume in each case. There thus exists a proportion of empty space of 75% by volume per reaction zone in each case in order to enable the liquid hydrocarbons formed to flow out freely.

Downstream of each reaction zone is a heat exchange zone in which the process gas and the liquid hydrocarbons formed are cooled at the same time, before they enter the next reaction zone.

The absolute inlet pressure of the process gas directly upstream of the first reaction zone is 30 bar. The length of the fixed catalyst beds, i.e. of the reaction zones, is selected such that a homogeneous temperature profile over the reaction zones is achieved. The exact values are listed in Table 1.

TABLE 1

Lengths of the reaction zones according to Example 1

| Reaction zone [—] | Length [m] |
|---|---|
| 1 | 2 |
| 2 | 2.08 |
| 3 | 2.16 |
| 4 | 2.26 |
| 5 | 2.38 |
| 6 | 2.52 |
| 7 | 2.68 |
| 8 | 2.88 |
| 9 | 3.2 |
| 10 | 3.6 |
| 11 | 4.4 |
| 12 | 6 |

Figure 1:
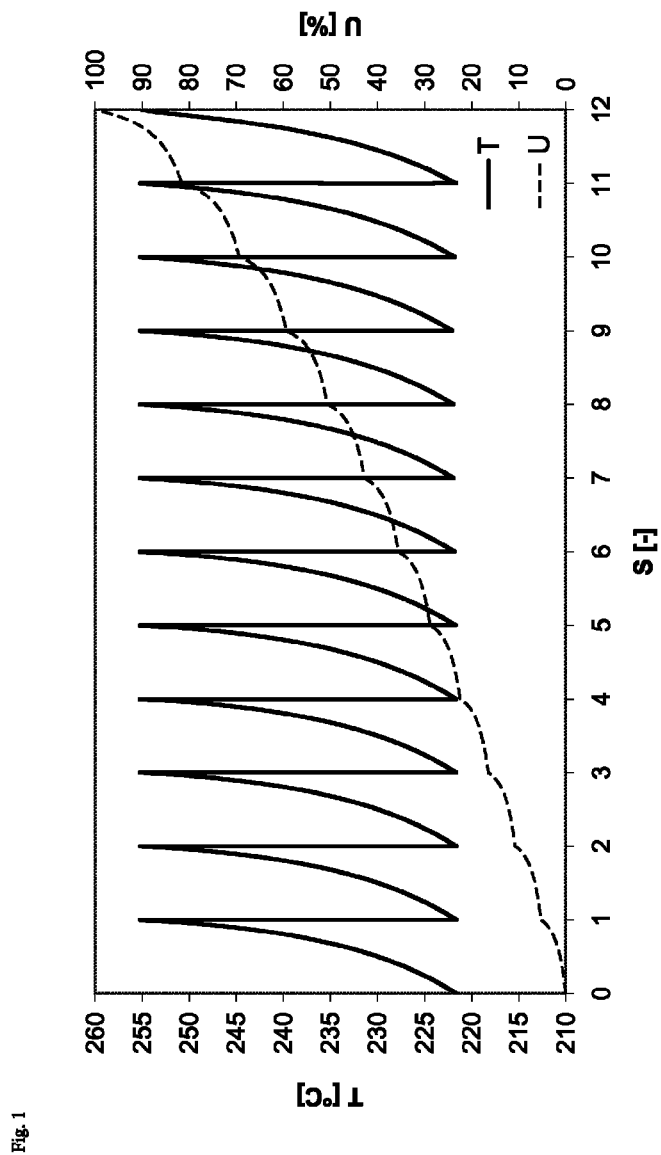
FIG. 1 shows reactor temperature (T) and conversion of carbon monoxide (U) over a number of 12 reaction zones (S) with downstream heat exchange zones (according to Example 1).

The results are shown in FIG. 1. In this figure, the individual reaction zones are shown on the X-axis, such that a spatial profile of the developments in the process becomes visible. On the left-hand Y-axis, the temperature of the process gas is specified, which is essentially identical to that of the liquid hydrocarbons. The temperature plot over the individual reaction zones is shown as a thick continuous line. On the right-hand Y-axis, the overall conversion of carbon monoxide is plotted. The plot of the conversion of carbon monoxide over the individual reaction zones is shown as a thin broken line.

It is evident that the inlet temperature of the process gas upstream of the first reaction zone is about 220° C. As a result of the exothermic reaction to give liquid hydrocarbons under adiabatic conditions, the temperature in the first reaction zone rises to 255° C., before the process gas and the liquid hydrocarbons are cooled again in the downstream heat exchange zone. The inlet temperature upstream of the next reaction zone is again about 220° C. As a result of exothermic adiabatic reaction, it rises again to about 255° C. The sequence of heating and cooling continues identically up to the 12th reaction zone.

A conversion of carbon monoxide of 99% is obtained. The selectivity obtained for liquid hydrocarbons comprising at least nine carbon atoms, based on carbon monoxide, is 40%. The space-time yield achieved, based on the volume of the reaction zone, is 31.88 kg$_{C>9}$/m$^3_{reaction\ zone}$h.

It can thus be shown that, by virtue of the very closely graduated temperature control by means of the process according to the invention, the full reaction of carbon monoxide with pure hydrogen in the manner of a multiphase Fischer-Tropsch synthesis in the presence of a heterogeneous catalyst can be operated safely, and that, at the same time, very advantageous conversions and selectivities, and also a very advantageous space-time yield, can be achieved.

Example 2

In this example, a process gas consisting of hydrogen and carbon monoxide with a molar ratio of 2.15 to 1 flows into a first of a total of 16 fixed catalyst beds composed of catalyst analogous to that of Example 1. The process thus comprises 16 reaction zones. Analogously to that of Example 1, the catalyst is present in each reaction zone in a proportion of 25% by volume.

Downstream of each reaction zone is a heat exchange zone in which the process gas and the liquid hydrocarbons formed are cooled at the same time, before they enter the next reaction zone.

The absolute inlet pressure of the process gas directly upstream of the first reaction zone is again 30 bar. The length of the fixed catalyst beds, i.e. of the reaction zones, is selected such that a substantially homogeneous temperature profile over the reaction zones is achieved. The exact values are listed in Table 2.

TABLE 2

Lengths of the reaction zones according to Example 2

| Reaction zone [—] | Length [m] |
|---|---|
| 1 | 1 |
| 2 | 1.03 |
| 3 | 1.06 |
| 4 | 1.09 |
| 5 | 1.13 |
| 6 | 1.18 |
| 7 | 1.23 |
| 8 | 1.29 |
| 9 | 1.36 |
| 10 | 1.44 |
| 11 | 1.54 |
| 12 | 1.65 |
| 13 | 1.82 |
| 14 | 2.1 |
| 15 | 2.6 |
| 16 | 2.7 |

Figure 2:
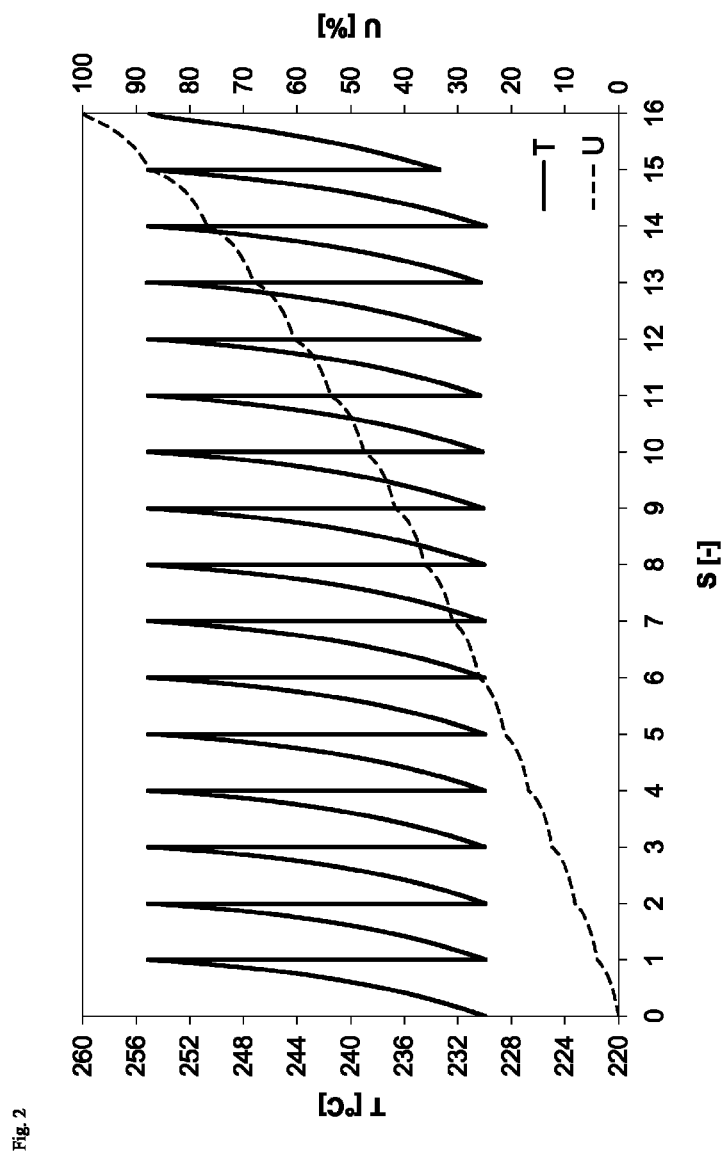
FIG. 2 shows reactor temperature (T) and conversion of carbon monoxide (U) over a number of 16 reaction zones (S) with downstream heat exchange zones (according to Example 2).

The results are shown in FIG. 2. In this figure, the individual reaction zones are shown on the X-axis, such that a spatial profile of the developments in the process becomes visible. On the left-hand Y-axis, the temperature of the process gas is specified, which is essentially identical to that of the liquid hydrocarbons. The temperature plot over the individual reaction zones is shown as a thick continuous line. On the right-hand Y-axis, the overall conversion of carbon monoxide is plotted. The plot of the conversion of carbon monoxide over the individual reaction zones is shown as a thin broken line.

It is evident that the inlet temperature of the process gas upstream of the first reaction zone is 230° C. As a result of the exothermic reaction to give liquid hydrocarbons under adiabatic conditions, the temperature in the first reaction zone rises to 255° C., before the process gas and the liquid hydrocarbons are cooled again in the downstream heat exchange zone. The inlet temperature upstream of the next reaction zone is again 230° C. As a result of exothermic adiabatic reaction, it rises again to about 255° C. The sequence of heating and cooling continues identically up to the 15th reaction zone. Thereafter, a somewhat lower cooling to only about 235° C. is provided upstream of the 16th reaction zone, since no such significant adiabatic temperature increase is expected from the small amount of remaining hydrogen and carbon monoxide present.

A conversion of carbon monoxide of 99% is obtained. The selectivity obtained for liquid hydrocarbons comprising at least nine carbon atoms, based on carbon monoxide, is 40%. The space-time yield achieved, based on the volume of the reaction zone, is this time, however, 45.52 $kg_{C>9}/m^3_{reaction\ zone}h$.

It can thus be shown that, by virtue of the very closely graduated temperature control by means of the process according to the invention, the full reaction of carbon monoxide with pure hydrogen in the manner of a multiphase Fischer-Tropsch synthesis in the presence of a heterogeneous catalyst can be operated safely, and that, at the same time, very advantageous conversions and selectivities can be achieved. In addition, closer graduation of an increased number of smaller adiabatic reaction zones with downstream heat exchange zone makes an even higher space-time yield achievable.

The invention claimed is:

1. Process for preparing liquid hydrocarbons from the process gases carbon monoxide and hydrogen, comprising a Fischer-Tropsch synthesis in the presence of heterogeneous catalysts, which is performed in 5 to 40 series-connected reaction zones in which the heterogeneous catalysts are present under adiabatic conditions at temperatures of 220° C. to 300° C., wherein downstream of each reaction zone is at least one heat exchange zone through which at least the process gases are passed and around each reaction zone is a thermal insulation zone.

2. Process according to claim 1, wherein the conversion is accomplished in 7 to 30 series-connected reaction zones.

3. Process according to claim 1, wherein the inlet temperature of the process gas entering the first reaction zone is from 10 to 260° C.

4. Process according to claim 1, wherein the absolute pressure at the inlet to the first reaction zone is between 10 and 70 bar.

5. Process according to claim 1, wherein the residence time of the process gas in all reaction zones together is between 10 and 700 s.

6. Process according to claim 1, wherein the catalysts are present in fixed bed arrangement.

7. Process according to claim 6, wherein the catalysts are present in the form of monoliths.

8. Process according to claim 7, wherein the monolith comprises channels having a diameter of 0.1 to 3 mm.

9. Process according to claim 1, wherein the process gases, optionally together with the liquid hydrocarbons, are passed through the at least one heat exchange zone.

10. Process according to claim 1, wherein the heat exchange zones are microstructured heat exchangers comprising fluid fluid-conducting channels with a hydraulic diameter between 50 μm and 5 mm.

11. Process according to claim 1, wherein as the process gases and/or liquid hydrocarbons are cooled in the heat exchange zones by the heat exchanger, steam is raised.

12. Process according to claim 11, wherein the steam is raised by partial evaporation.

13. Process according to claim 1, wherein the maximum outlet temperature of the process gas from the reaction zones is within a range from 220° C. to 300° C.

14. Process according to claim 13, wherein the maximum outlet temperature of the process gas from the reaction zones is within a range from 240° C. to 280° C.

15. Process according to claim 1, wherein the maximum outlet temperature of the process gas from the reaction zones is within a range from 250° C. to 260° C.

16. Process according to claim 1, wherein in the first reaction zone a catalyst is used, which has under otherwise identical conditions a less activity for the reaction of carbon monoxide with hydrogen compared to the catalysts used in the other reaction zones.

17. Process according to claim 1, wherein the same catalysts are used in each reaction zone.

* * * * *